(12) United States Patent
Umeno

(10) Patent No.: US 9,004,560 B2
(45) Date of Patent: Apr. 14, 2015

(54) ROBOT HAND AND ROBOT

(71) Applicant: Kabushiki Kaisha Yaskawa Denki, Kitakyushu-shi (JP)

(72) Inventor: Makoto Umeno, Kitakyushu (JP)

(73) Assignee: Kabushiki Kaisha Yaskawa Denki, Kitakyushu-Shi (JP)

( * ) Notice: Subject to any disclaimer, the term of this patent is extended or adjusted under 35 U.S.C. 154(b) by 0 days.

(21) Appl. No.: 14/109,857

(22) Filed: Dec. 17, 2013

(65) Prior Publication Data

US 2014/0102239 A1 Apr. 17, 2014

Related U.S. Application Data

(63) Continuation of application No. PCT/JP2012/066408, filed on Jun. 27, 2012.

(30) Foreign Application Priority Data

Jun. 28, 2011 (JP) ................................. 2011-143456

(51) Int. Cl.
*B66C 1/42* (2006.01)
*B25J 15/00* (2006.01)
(Continued)

(52) U.S. Cl.
CPC .......... *B25J 15/0038* (2013.01); *B25J 15/0033* (2013.01); *B25J 9/0087* (2013.01); *B25J 15/0253* (2013.01); *G01N 35/0099* (2013.01); *B25J 18/00* (2013.01); *Y10S 901/31* (2013.01)

(58) Field of Classification Search
USPC ............. 294/119.1, 86.4, 902, 219, 213, 907, 294/192, 207; 414/741; 901/30–31, 37; 269/25, 33
See application file for complete search history.

(56) References Cited

U.S. PATENT DOCUMENTS 4,714,865 A * 12/1987 Chin et al. ..................... 318/563
5,328,224 A * 7/1994 Jacobsen et al. .............. 294/104
(Continued)

FOREIGN PATENT DOCUMENTS

| EP | 0703457 | 3/1996 |
| EP | 1741488 | 1/2007 |

(Continued)

OTHER PUBLICATIONS

Chinese Office Action for corresponding CN Application No. 201280031648.4, Jun. 27, 2014.
(Continued)

*Primary Examiner* — Stephen Vu
(74) *Attorney, Agent, or Firm* — Mori & Ward, LLP

(57) ABSTRACT

A robot hand includes a pair of bits and holds a microtube by causing the pair of bits to perform an opening-closing operation. The pair of bits has a lug that comes into contact with an outer peripheral surface of a container body or a cap portion of the microtube, and a rectangular recess in which parts of the cap portion and a flange of the microtube are inserted while the lug is in contact with an outer peripheral surface of the microtube. The rectangular recess includes surfaces between which the cap portion and the flange are disposed. The pair of bits is closed while a corner of the rectangular recess is in contact with the outer peripheral surface of the container body to retain the microtube in an orientation different from that in the state in which the cap portion is inserted in the rectangular recess.

7 Claims, 10 Drawing Sheets

(51) Int. Cl.
- *B25J 9/00* (2006.01)
- *B25J 15/02* (2006.01)
- *G01N 35/00* (2006.01)
- *B25J 18/00* (2006.01)

(56) References Cited

U.S. PATENT DOCUMENTS

| | | | |
|---|---|---|---|
| 5,382,408 A | 1/1995 | Perlman | |
| 5,863,086 A * | 1/1999 | Christenson | 294/106 |
| 7,140,655 B2 * | 11/2006 | Kesil et al. | 294/104 |
| 7,422,411 B2 * | 9/2008 | Downs et al. | 414/741 |
| 2005/0204848 A1 | 9/2005 | Kariyazaki et al. | |
| 2011/0120253 A1 | 5/2011 | Tara et al. | |

FOREIGN PATENT DOCUMENTS

| | | |
|---|---|---|
| EP | 2287621 | 2/2011 |
| JM | 2010-000563 | 1/2010 |
| JP | 61-189457 | 8/1986 |
| JP | 64-061667 | 3/1989 |
| JP | 03-226484 | 10/1991 |
| JP | 04-198867 | 7/1992 |
| JP | 07-055813 | 3/1995 |
| JP | 2008-054690 | 3/2008 |
| JP | 2010-000563 | 1/2010 |

OTHER PUBLICATIONS

International Search Report for corresponding International Application No. PCT/JP2012/066408, Sep. 11, 2012.

Written Opinion for corresponding International Application No. PCT/JP2012/066408, Sep. 11, 2012.

Japanese Office Action for corresponding JP Application No. 2013-522901, Sep. 2, 2014.

Extended European Search Report for corresponding EP Application No. 12804758.6-1553, Feb. 18, 2015.

* cited by examiner

US 9,004,560 B2

ROBOT HAND AND ROBOT

CROSS-REFERENCE TO RELATED APPLICATIONS

The present application is a continuation application of PCT/JP2012/066408, filed Jun. 27, 2012, which claims priority to Japanese Patent Application No. 2011-143456, filed Jun. 28, 2011. The contents of these applications are incorporated herein by reference in their entirety.

BACKGROUND OF THE INVENTION

1. Field of the Invention

The present invention relates to a robot hand and a robot.

2. Description of the Related Art

In the biological and medical fields, analyses using materials derived from living organisms as samples have been performed. The materials derived from living organisms are biologic materials, such as blood and urine, cultured cell suspensions, etc., and are often liquid materials. To analyze such a liquid material, the liquid material is contained in a small centrifuging tube (microtube), and subjected to centrifugal separation or stored.

In recent years, systems have been proposed which include a robot that operates an analytical instrument or the like for the purpose of quickly analyzing many samples or analyzing samples harmful to humans. For example, PTL 1 describes an automatic cell-culturing device including instruments, such as an incubator and a centrifugal separator, necessary for a culturing operation and a robot for operating the instruments. The automatic cell-culturing device described in Japanese Unexamined Patent Application Publication No. 2008-54690 includes a robot hand for operating the instruments necessary for the culturing operation, and the culturing operation is performed not manually but by the robot that manipulates the robot hand.

In addition, systems including robots that convey microtubes have also been proposed. Such a system generally includes a robot that conveys microtubes between a physicochemical instrument for processing samples contained in the microtubes and a delivery table and a robot that conveys the microtubes between delivery tables.

When a system including a plurality of physicochemical instruments designed on the assumption that microtubes are manually attached and detached to and from the physicochemical instruments is to be established, a plurality of robot hands optimized in accordance with the orientations in which the microtubes are to be set in the physicochemical instruments may be selectively used. However, the step of exchanging the robot hands causes a loss of process time, and there is a problem that the overall process time will be increased.

SUMMARY OF THE INVENTION

According to an aspect of the present disclosure, a robot hand includes a pair of bits and holds a microtube by causing the pair of bits to perform an opening-closing operation. The pair of bits includes a projection that comes into contact with an outer peripheral surface of a container body of the microtube or an outer peripheral surface of a cap portion of the microtube as a result of the opening-closing operation, and a recess in which both a part of the cap portion and a part of a flange of the microtube are inserted while the projection is in contact with the outer peripheral surface of the container body. The recess has a rectangular shape and includes a pair of surfaces between which the cap portion and the flange are disposed. The pair of bits is closed while a corner of the recess is in contact with the outer peripheral surface of the container body to retain the microtube in an orientation different from an orientation of the microtube in the state in which the cap portion is inserted in the recess.

DESCRIPTION OF THE EMBODIMENTS

Figure 1:
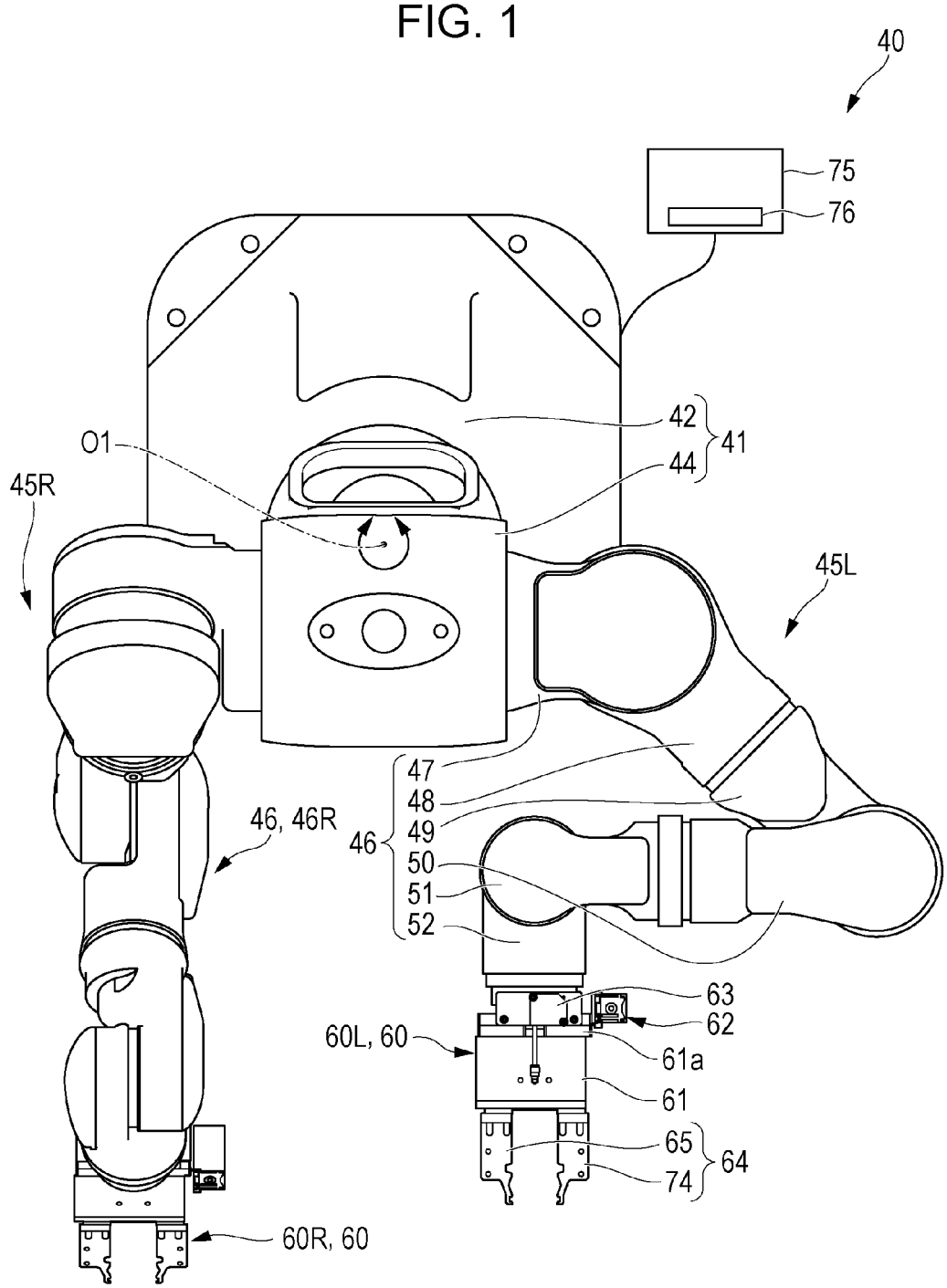
FIG. 1 is a plan view of a robot including robot hands according to an embodiment of the present disclosure.
Figure 2:
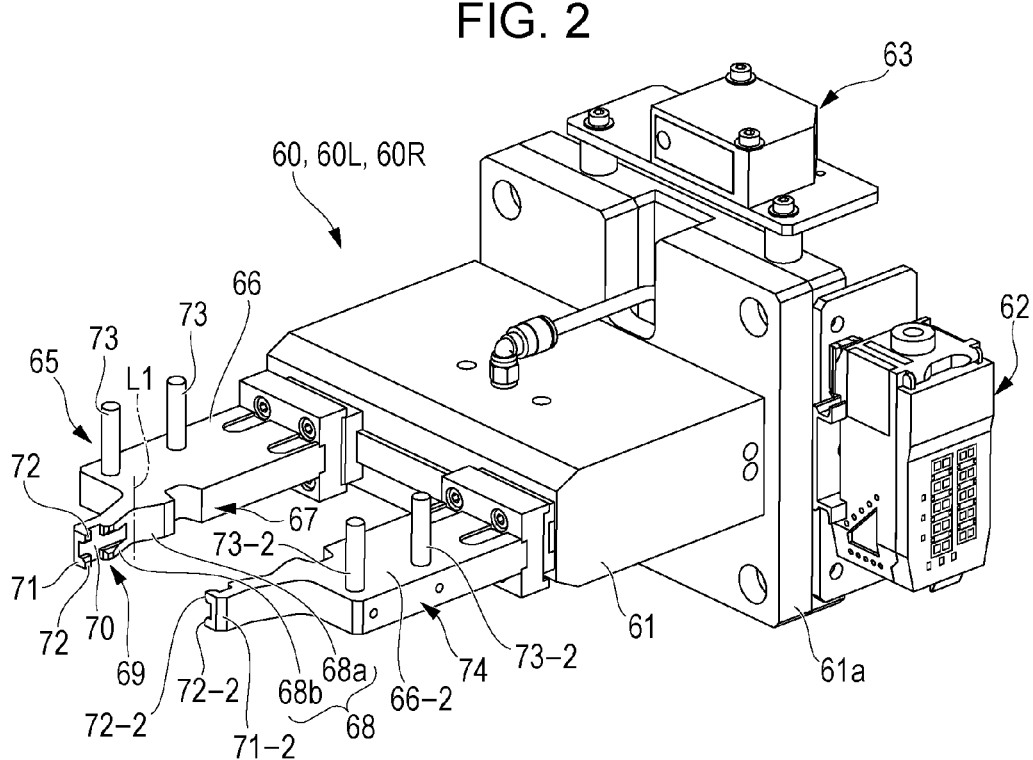
FIG. 2 is a perspective view of each robot hand included in the robot.
Figure 3:
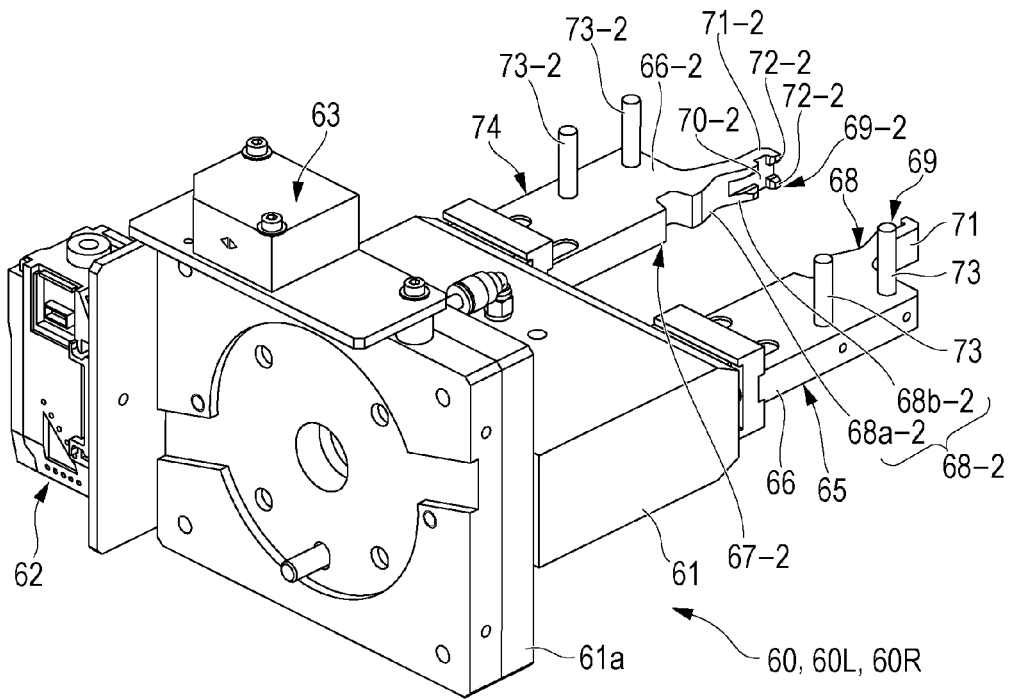
FIG. 3 is a perspective view of the robot hand included in the robot.
Figure 4:
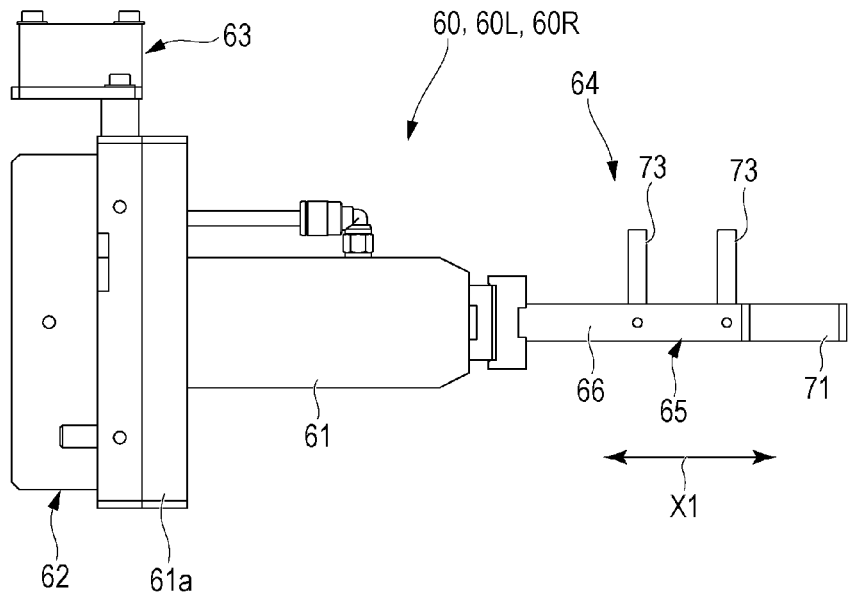
FIG. 4 is a front view of the robot hand.

Robot hands and a robot according to an embodiment of the present disclosure will now be described. FIG. 1 is a plan view of the robot including the robot hands according to the present embodiment. FIGS. 2 and 3 are perspective views of each robot hand included in the robot. FIGS. 4, 5, 6, 7, 8, and 9 are a front view, a plan view, a bottom view, a left side view, a right side view, and a rear view, respectively, of the robot hand.

As illustrated in FIG. 1, the robot 40 includes a body 41, a first arm 45L, a second arm 45R, and a driver 75.

The body 41 includes a fixed portion 42 that is fixed to, for example, the floor and a swing portion 44 that is connected to the fixed portion 42.

The fixed portion 42 and the swing portion 44 are relatively rotatable around a predetermined axis. The swing portion 44 is caused to swing relative to the fixed portion 42 in response to a drive signal transmitted from the driver 75.

The first arm 45L includes an articulated arm 46 that is provided on the body 41 and has six or more degrees of freedom and a robot hand 60 provided at the distal end of the articulated arm 46.

The articulated arm 46 includes a first frame 47, a second frame 48, a third frame 49, a fourth frame 50, a fifth frame 51, and a sixth frame 52 in that order from the body-41 side.

In the present embodiment, the first-frame-47 side of the articulated arm 46 in a linear state is referred to as the proximal side of the articulated arm 46, and the sixth-frame-52 side of the articulated arm 46 in the linear state is referred to as the distal side of the articulated arm 46.

An existing connection structure may be adopted as the connection structure of the frames included in the articulated arm 46. For example, an articulated manipulator disclosed in International Publication No. 2007/037131 may be used as the articulated arm 46 of the present embodiment. An example of a connection structure of the frames will now be described.

The first frame 47 has a first rotation axis that extends in a horizontal direction from the body 41, and rotates around the first rotation axis with respect to the body 41. The second frame 48 rotates around a second rotation axis, which is orthogonal to the first rotation axis, with respect to the first frame 47. The third frame 49 rotates around a third rotation axis, which is orthogonal to the second rotation axis, with respect to the second frame 48. The fourth frame 50 rotates around a fourth rotation axis, which is orthogonal to the third rotation axis, with respect to the third frame 49. The fifth frame 51 rotates around a fifth rotation axis, which is orthogonal to the fourth rotation axis, with respect to the fourth frame 50. The sixth frame 52 rotates around a sixth rotation axis, which is orthogonal to the fifth rotation axis, with respect to the fifth frame 51. The above-described robot hand 60 is connected to the distal end of the sixth frame 52 such that the robot hand 60 is rotatable around a seventh rotation axis, which is orthogonal to the sixth rotation axis.

In the present embodiment, the driver 75 is capable of causing the articulated arm 46 to perform the rotations around the first to seventh rotation axes, which are seven rotation axes in total, individually. In other words, the articulated arm 46 according to the present embodiment has seven degrees of freedom. If the articulated arm 46 has six degrees of freedom, the distal end of the articulated arm 46 can be positioned in a desired orientation in a three-dimensional space. The robot 40 of the present embodiment has seven degrees of freedom including a single redundant axis in addition to six degrees of freedom. Therefore, the distal end of the articulated arm 46 can be moved in a smaller space than in the case where the number of degrees of freedom is six.

As illustrated in FIG. 1, in the present embodiment, the first arm 45L and the second arm 45R include robot hands 60 (first robot hand 60L and second robot hand 60R) having the same shape.

Each robot hand 60 includes a gripper 61, a hold sensor 62, and a laser sensor 63. The gripper 61 causes a pair of bits 64 to move toward and away from each other in a direction orthogonal to the rotation axis (the above-described seventh rotation axis) around which the robot hand 60 rotates with respect to the sixth frame 52. The hold sensor 62 detects a reactive force generated when an object to be held is held by the gripper 61. The laser sensor 63 rotates around the seventh rotation axis together with the gripper 61, and includes a laser source and an optical sensor.

The gripper 61 is fixed to the sixth frame 52 with a plate-shaped base 61a interposed therebetween. The robot hand 60 can be detachably attached to the sixth frame 52 at a position between the base 61a and the sixth frame 52. In the present embodiment, it is not essential that the robot hand 60 be replaceable with a robot hand having another structure for another operation.

The gripper 61 is an electric gripper that receives electric power to perform an opening-closing operation. Since the reactive force is detected by the hold sensor 62, the gripper 61 is capable of causing the pair of bits 64 to hold an object to be held at a predetermined force or pressing the object held by the pair of bits 64 against another object at a predetermined pressing force.

The hold sensor 62 is fixed to the base 61a and is electrically connected to the gripper 61 with a signal line (not shown).

The laser sensor 63 is connected to the base 61a. The laser sensor 63 is provided to switch the operation of the driver 75 when a predetermined color marker is detected.

The pair of bits 64 includes a first bit 65 and a second bit 74 that are plane-symmetrical to each other in a state in which they oppose each other. In the following description, components of the first bit 65 will be mainly explained. Components of the second bit 74 are denoted by reference numerals corresponding to those of the corresponding components (reference numerals with an index "−2" attached) as necessary, and explanations thereof are thus omitted.

As illustrated in FIGS. 2 to 9, the first bit 65 includes a main body 66 that is connected to the gripper 61 and holding members 73 that are fixed to the main body 66.

The main body 66 is, for example, a substantially plate-shaped member that is formed by cutting a metal plate. The proximal end of the main body 66 is connected to the gripper 61, and the main body 66 extends toward the distal side of the articulated arm 46. The gripper 61 translates the proximal end of the main body 66 so that the main body 66 moves toward and away from the second bit 74 while being parallel to the second bit 74, thereby performing an opening-closing operation.

The dimension of the main body 66 in the direction from the proximal end to the distal end of the main body 66 is preferably as small as possible within a range in which the object to be held can be held appropriately. This is because the smaller the main body 66, the easier the main body 66 can be moved within the workspace. In addition, in the present embodiment, the proximal end of the main body 66 at which force is applied by the gripper 61 to move the main body 66 serves as a point of application and a fulcrum, and the distal end of the main body 66 at which the object to be held is held serves as a point of load. Therefore, as the dimension of the main body 66 in the direction from the proximal end to the distal end of the main body 66 is reduced, the distance between the fulcrum and the point of load can be reduced. As a result, the positional accuracy of the distal end of the main body 66 can be increased.

A large-diameter holder 68 and a small-diameter holder 69 are arranged on an external surface of the main body 66 that faces the second bit 74 (hereinafter referred to as an "inner surface 67") in that order in the direction from the proximal end to the distal end.

The large-diameter holder 68 is shaped such that the inner surface 67 is recessed in an opening direction of the pair of bits 64. In the large-diameter holder 68, the inner surface 67 has a bent shape such that two flat surfaces (a first surface 68a and a second surface 68b) have a line of intersection L1 that extends in the thickness direction of the main body 66.

The shape of the large-diameter holder 68 is optimized so that a columnar or cylindrical object can be held while being positioned such that a central axis of the object is parallel to the above-described line of intersection L1. In other words, the columnar or cylindrical object is held such that the first and second surfaces simultaneously contact the outer peripheral surface thereof. At this time, owing to the force applied by the gripper 61, the columnar or cylindrical object is held while being positioned such that the central axis thereof is parallel to the above-described line of intersection L1.

The small-diameter holder 69 includes a rectangular recess 70 (first recess) that is disposed on the distal side of the large-diameter holder 68 and in which the inner surface 67 is recessed in a rectangular shape in the opening direction of the pair of bits 64 and a lug 71 that is disposed on the distal side of the rectangular recess 70.

The dimension of the open side of the rectangular recess 70 in the direction from the proximal end to the distal end of the main body 66 is such that a rim of a cap portion 19b of a microtube 19 and a rim of a flange 19d of the microtube 19 can be removably inserted into the rectangular recess 70 with a small clearance. In addition, the depth of the rectangular recess 70 is set such that the tip of the lug 71 can contact the outer peripheral surface of a container body 19a of the microtube 19 in the state in which the rim of the cap portion 19b and the rim of the flange 19d of the microtube 19 are inserted in the rectangular recess 70.

The lug 71 is shaped such that a central portion thereof is cut in a rectangular shape when viewed in the direction from the distal end to the proximal end of the main body 66. The lug 71 is capable of holding the outer peripheral surfaces of both the cap portion 19b and the flange 19d of the microtube 19. In addition, the lug 71 is also capable of holding the outer peripheral surface of the container body 19a of the microtube 19. The tip of the lug 71 that is viewed in the direction from the distal end to the proximal end of the main body 66 has projections 72 that contact the outer peripheral surface of a columnar or cylindrical object, such as the microtube 19, to hold the object.

The lug 71 may be shaped such that the central portion thereof is cut in a V-shape instead of being cut in a rectangular shape.

When the lug 71 is viewed in the thickness direction of the main body 66, the inner surface 67 of the lug 71 is parallel to a straight line that extends from the proximal end to the distal end of the main body 66 (hereinafter referred to as "longitudinal axis X1"). A boundary portion between the lug 71 and the rectangular recess 70 extends obliquely in a direction that crosses both a straight line that extends in the opening-closing direction of the pair of bits 64 (hereinafter referred to as a "width axis Y1") and the above-described longitudinal axis X1 when viewed in the thickness direction of the main body 66.

The holding members 73 are optimized to hold a culture vessel 18. The holding members 73 are rod-shaped members that extend in the thickness direction of the main body 66 from one of the surfaces of the main body 66 in the thickness direction (hereinafter referred to as a "front surface of the main body 66"). The holding members 73 are disposed at positions offset from the inner surface 67 of the main body 66 in the opening direction of the pair of bits 64.

Two of the holding members 73 are arranged parallel to each other on each of the pair of bits 64. The two holding members 73 provided on the first bit 65 are arranged such that central axes thereof are both on a straight line that is parallel to the longitudinal axis X1 when viewed in the thickness direction of the main body 66.

The dimension of each holding member 73 from the front surface of the main body 66 to the tip of the holding member 73 in the thickness direction of the main body 66 is equal to or slightly greater than the external dimension of the culture vessel 18 in the depth direction of the culture vessel 18. The two holding members 73 have the same external dimensions.

The second bit 74 includes a large-diameter holder 68-2 and a small-diameter holder 69-2 that are plane-symmetrical to the large-diameter holder 68 and the small-diameter holder 69, respectively, which are formed on the first bit 65. The small-diameter holder 69-2 has a rectangular recess 70-2 (second recess) that is plane-symmetrical to the rectangular recess 70 in the first bit 65. In addition, the second bit 74 includes two of the above-described holding members 73.

The distal ends of the four holding members 73 included in the first bit 65 and the second bit 74 are on the same imaginary plane.

Figure 10:
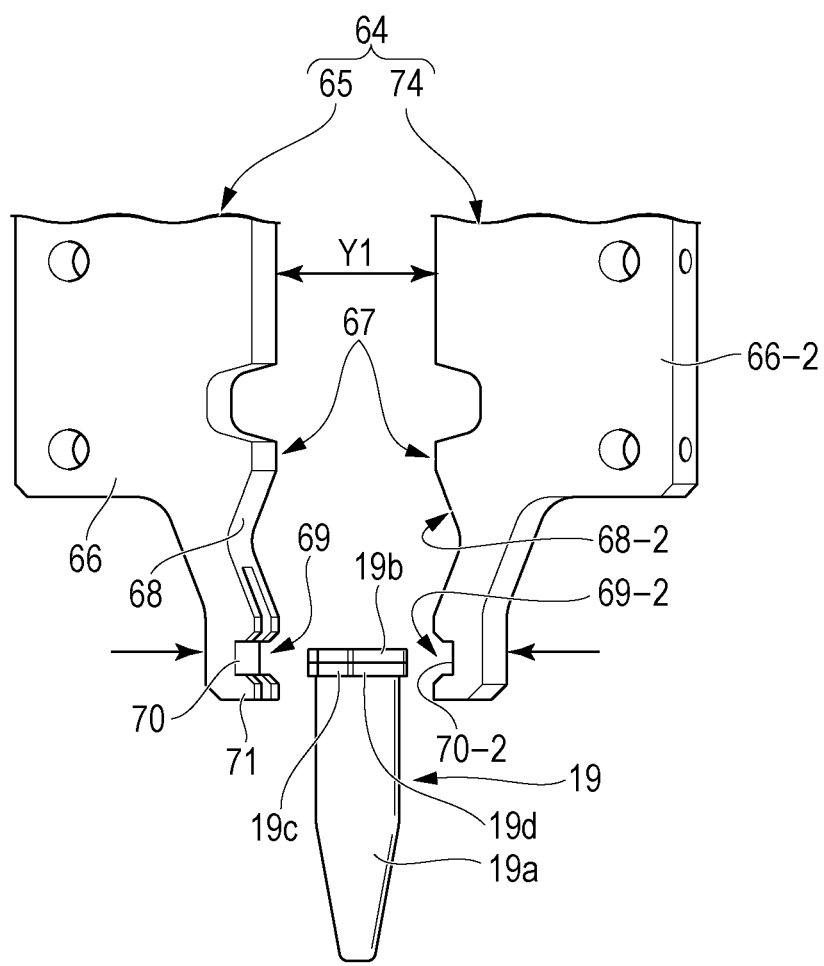
FIG. 10 is a diagram for describing the operation of the robot hand.

As illustrated in FIG. 10, in the present embodiment, the dimensions of both the rectangular recess 70 (first recess) of the first bit 65 and the rectangular recess 70-2 (second recess) of the second bit 74 are set such that the rectangular recesses 70 and 70-2 are capable of receiving the flange 19d and a hinge 19c of the microtube 19 in the state in which the cap portion 19b is closed.

As illustrated in FIG. 1, the second arm 45R is symmetrical to the first arm 45L, and includes an articulated arm 46R having a connection structure that is similar to that of the first arm 45L and a second robot hand 60R having the same shape as that of the first robot hand 60L. The structure of the second arm 45R is the same as that of the first arm 45L except that the shape of the second arm 45R is symmetrical to the shape of the first arm 45L. In this specification, components of the second arm 45R are denoted by reference numerals corresponding to those of the corresponding components (reference numerals with an index "R" attached), and explanations thereof are thus omitted.

The robot hand 60 included in the second arm 45R (second robot hand 60R) is identical to the robot hand 60 included in the first arm 45L (first robot hand 60L). Therefore, components thereof are denoted by reference numerals corresponding to those of the corresponding components (reference numerals with an index "R" attached), and explanations thereof are thus omitted.

The driver 75 illustrated in FIG. 1 includes actuators (not shown) for operating the body 41, the first arm 45L, and the second arm 45R, and a controller 76 that outputs predetermined drive signals to the actuators.

In the present embodiment, electric motors having servo mechanisms are used as the actuators. Therefore, compared to the case where fluid drive actuators, such as air cylinders, are used, the positional accuracy can be increased and vibrations generated when the driving operation is started and ended can be reduced.

The controller 76 can be connected to a controller for inputting drive sequences of the body 41, the first arm 45L, and the second arm 45R. The robot 40 can be caused to memorize the operation sequences by a teaching process. The robot 40 may be caused to memorize the operation sequences by a so-called direct teaching process. The controller 76 drives the actuators by generating drive signals to be output to the actuators on the basis of the memorized operation sequences. In other words, the robot 40 causes the driver 75 to drive the actuators by a teaching-playback process based on the position and shape of a physicochemical instrument, thereby playing back the operations memorized by the teaching process.

The controller 76 detects the relative position between the first robot hand 60L and the second robot hand 60R on the basis of the information of displacements obtained by the servo mechanisms of the actuators provided on the first arm 45L and the second arm 45R, and causes the first robot hand 60L and the second robot hand 60R to perform a cooperative operation in accordance with the above-described teaching process.

The controller 76 also receives a predetermined output of the laser sensor 63, and moves each robot hand 60 to a position corresponding to the position of the physicochemical instrument.

The operations of the robot 40 and each robot hand 60 will now be described. FIGS. 10 to 13 are diagrams for describing the operation of the robot hand.

First, an example in which the microtube 19 placed on a tube rack is conveyed to another tube rack will be described.

The robot 40 illustrated in FIG. 1 causes the gripper 61 to open the pair of bits 64 of the first robot hand 60L. Then, in the state in which the longitudinal axis X1 of the first robot hand 60L extends in the vertical direction, the pair of bits 64 is moved toward the microtube 19 placed on the tube rack from the sides of the microtube 19, as illustrated in FIG. 10. The robot 40 stops the movement of the first robot hand 60L at a position where the cap portion 19b of the microtube 19 can be inserted into the rectangular recesses 70 formed in the pair of bits 64.

Then, the robot 40 causes the gripper 61 to close the pair of bits 64. When the lugs 71 of the pair of bits 64 contact the outer peripheral surface of the container body 19a of the microtube 19, the reactive force is detected by a contact sensor. When the contact sensor detects the reactive force, the robot 40 stops the operation of closing the pair of bits 64 performed by the gripper 61. At this time, the robot 40 holds the microtube 19 such that the cap portion 19b and the flange 19d are inserted in the rectangular recesses 70 while the hinge 19c of the microtube 19 is positioned between the pair of bits 64. In addition, the outer peripheral surface of the microtube 19 is held by the lugs 71.

The robot 40 causes the first robot hand 60L to move upward to pull the microtube 19 out of the tube rack. Then, the robot 40 moves the first robot hand 60L to the other tube rack and places the microtube 19 on the other tube rack.

The microtube 19 may instead be held softly by controlling the positions of the pair of bits 64 so that small gaps are provided between the outer peripheral surface of the container body 19a and the lugs 71. In this case, when the microtube 19 is brought into contact with a mixer (for example, a Vortex mixer (registered trademark)) for stirring liquid or the like contained in the microtube 19, the microtube 19 receives vibrations from the mixer and moves even when the first robot hand 60L is not moved.

Next, an example in which the robot hand 60 opens the cap of the microtube 19 will be described.

Figure 11:
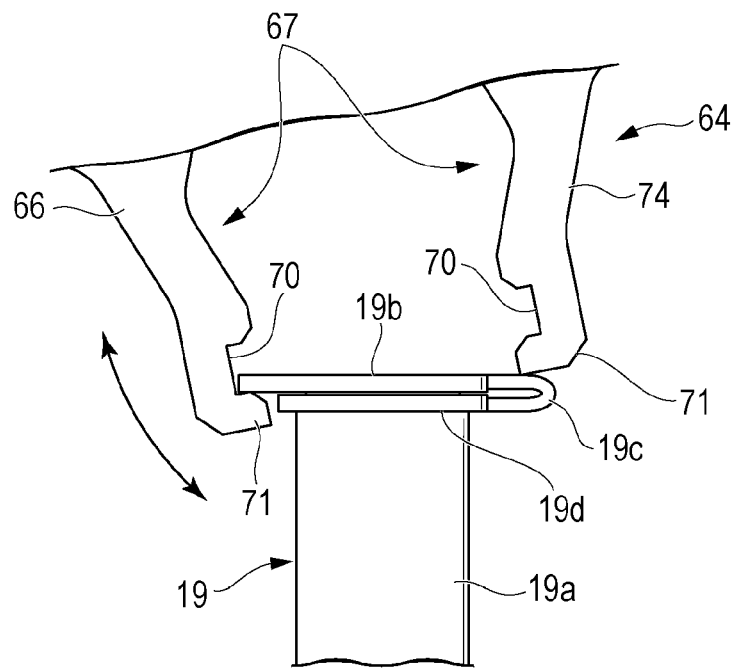
FIG. 11 is a diagram for describing the operation of the robot hand.

As illustrated in FIG. 11, the robot 40 sets the longitudinal axis X1 of the pair of bits 64 so that it is slightly at an angle with respect to the vertical direction. The distal end of one of the first bit 65 and the second bit 74 is brought into contact with the top portion of the hinge 19c, and a part of the cap portion 19b that opposes the hinge 19c is inserted into the rectangular recess of the other one of the first bit 65 and the second bit 74 (into the rectangular recess 70 or the rectangular recess 70-2). The robot 40 causes the robot hand 60 to rotate around the hinge 19c while the cap portion 19b and the hinge 19c are retained by the rectangular recesses 70 and 70-2 in the above-described manner, so that the cap portion 19b is pulled off from the container body 19a. Accordingly, the cap portion 19b is pivoted around the hinge 19c and the cap of the microtube 19 is slightly opened.

Figure 12:
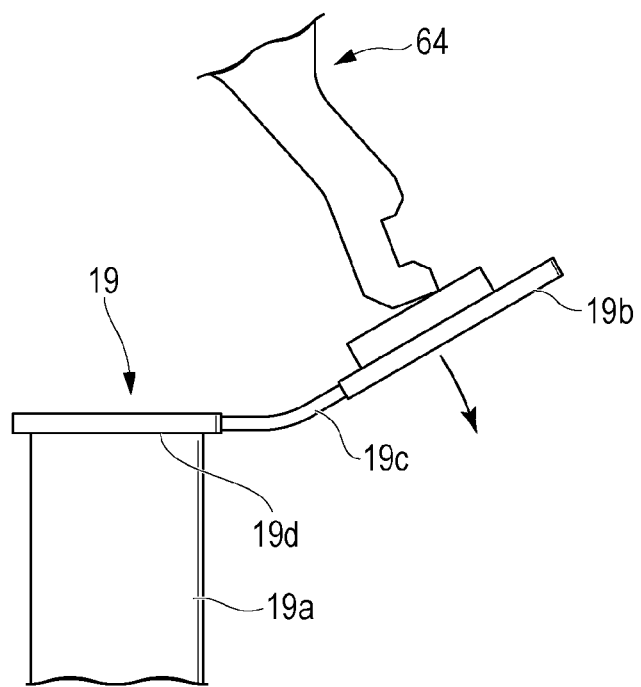
FIG. 12 is a diagram for describing the operation of the robot hand.

Then, as illustrated in FIG. 12, the robot 40 (see FIG. 1) pushes the inner surface of the cap that has been opened with the pair of bits 64 and stretches the hinge 19c that has been bent and creased, thereby fully opening the cap. The state in which the cap is fully opened is the state in which the opening at the top of the container body 19a is not covered with the cap portion 19b.

Next, an example in which the robot hand 60 closes the cap of the microtube 19 will be described.

The robot 40 brings the pair of bits 64 connected to the gripper 61 of the second robot hand 60R into contact with the microtube 19 having the cap that is open, and pushes the cap portion 19b with the pair of bits 64 to bend the hinge 19c of the microtube 19. The cap portion 19b is further pushed by the pair of bits 64 so that the cap portion 19b is pushed into the container body 19a.

Thus, the cap of the microtube 19 is closed.

Next, an example in which the robot hand 60 holds a rim portion of the cap of the microtube 19 will be described.

Figure 13:
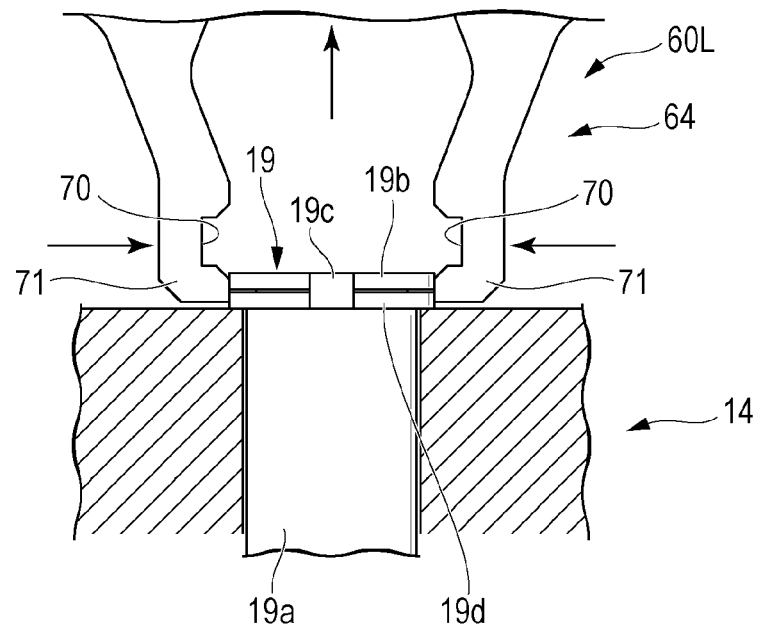
FIG. 13 is a diagram for describing the operation of the robot hand.

As illustrated in FIG. 13, the first robot hand 60L holds the microtube 19 in such a manner that the lugs 71 of the pair of bits 64 contact the outer peripheral surfaces of the cap portion 19b and the flange 19d of the microtube 19. In this state, the projections 72 of the lugs 71 engage with the rim of the cap portion 19b.

According to this example, even when, for example, the microtube 19 is placed on a rotor of a centrifugal separator and is held in such a manner that all parts thereof excluding the cap portion 19b, the hinge 19c, and the flange 19d are placed in a hole, the microtube 19 can be taken out of the hole without applying vibrations thereto.

Next, an example in which the microtube 19 is passed between the first robot hand 60R and the second robot hand 60L will be described.

Figure 14:
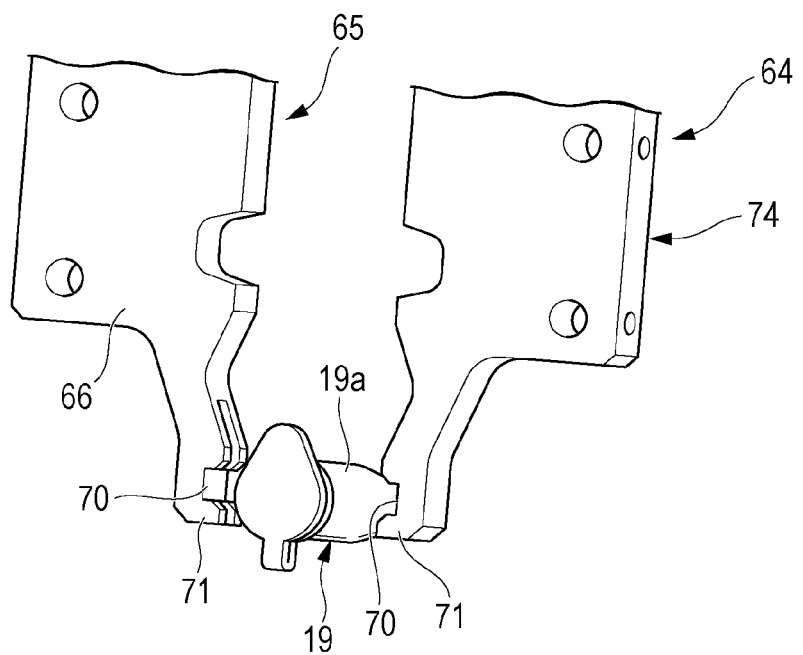
FIG. 14 is a diagram for describing the operation of the robot hand.

The robot 40 causes the pair of bits 64 of the second robot hand 60R to hold the microtube 19 placed on a tube rack from above (see FIG. 10). Then, as illustrated in FIG. 14, the microtube 19 that is held by the second robot hand 60R at a position near the cap portion 19b and the flange 19d is held by the pair of bits 64 of the first robot hand 60L such that the outer peripheral surface of the container body 19a is clamped between the rectangular recesses 70 that oppose each other. Thus, the microtube 19 is passed from the second robot hand 60R to the first robot hand 60L.

The microtube 19 can be passed from the second robot hand 60R to the first robot hand 60L while the swing portion 44 is performing a swinging motion. Therefore, the manner in which the microtube 19 is held can be changed while the microtube 19 is being conveyed from one physicochemical instrument to another.

Next, an example in which a culture vessel for culturing cells is held will be described.

Figure 15:
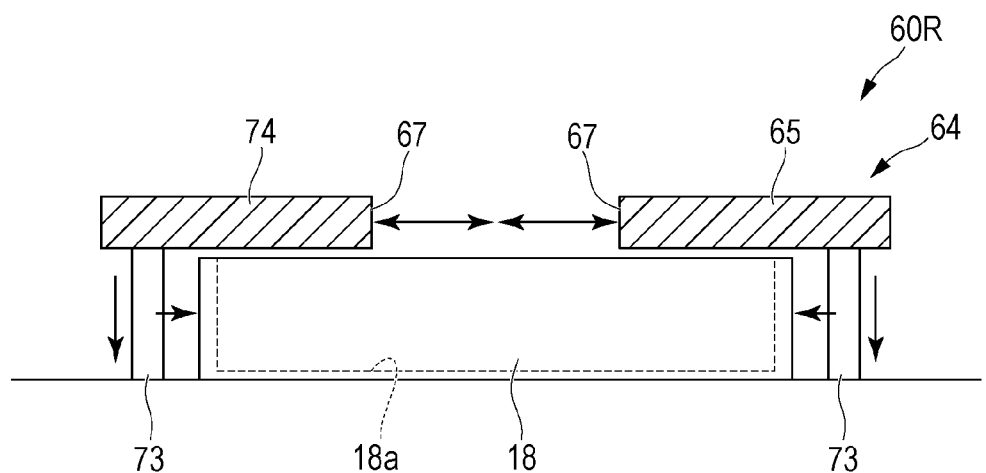
FIG. 15 is a diagram for describing the operation of the robot hand.

As illustrated in FIG. 15, the robot 40 causes the second robot hand 60R to hold the culture vessel 18 in which adhesive cells are cultured. In this case, the robot 40 controls the orientation of the pair of bits 64 so that the distal ends (tips) of the holding members 73 point downward.

The robot 40 causes the gripper 61 of the second robot hand 60R to open the pair of bits 64. At this time, the gripper 61 opens the pair of bits 64 to the limit of the operational range thereof. The robot 40 arranges the pair of bits 64 so that the four holding members 73 surround the outer periphery of the culture vessel 18, and moves the second robot hand 60R downward until the distal ends of the four holding members 73 come into contact with the surface on which the culture vessel 18 is placed. In the state in which the distal ends of the four holding members 73 are in contact with the surface on which the culture vessel is placed, the robot 40 causes the gripper 61 to close the pair of bits 64. When the pair of bits 64 is closed, the distal ends of the four holding members 73 provided on the pair of bits 64 come into contact with the outer periphery of the bottom of the culture vessel 18 and hold the outer periphery of the bottom portion of the culture vessel 18. In addition, in a region on the proximal side of the distal ends of the holding members 73 (region closer to the attachment portions of the pair of bits 64 than the distal ends of the holding members 73), the outer peripheral surface of the culture vessel 18 is held by the outer peripheral surfaces of the holding members 73.

In this example, the culture vessel 18 has no cover. In the case where the vessel has a cover, the cover can be removed by the above-described operation.

Next, an example in which the culture vessel 18 is passed between the first robot hand 60L and the second robot hand 60R will be described.

Figure 16:
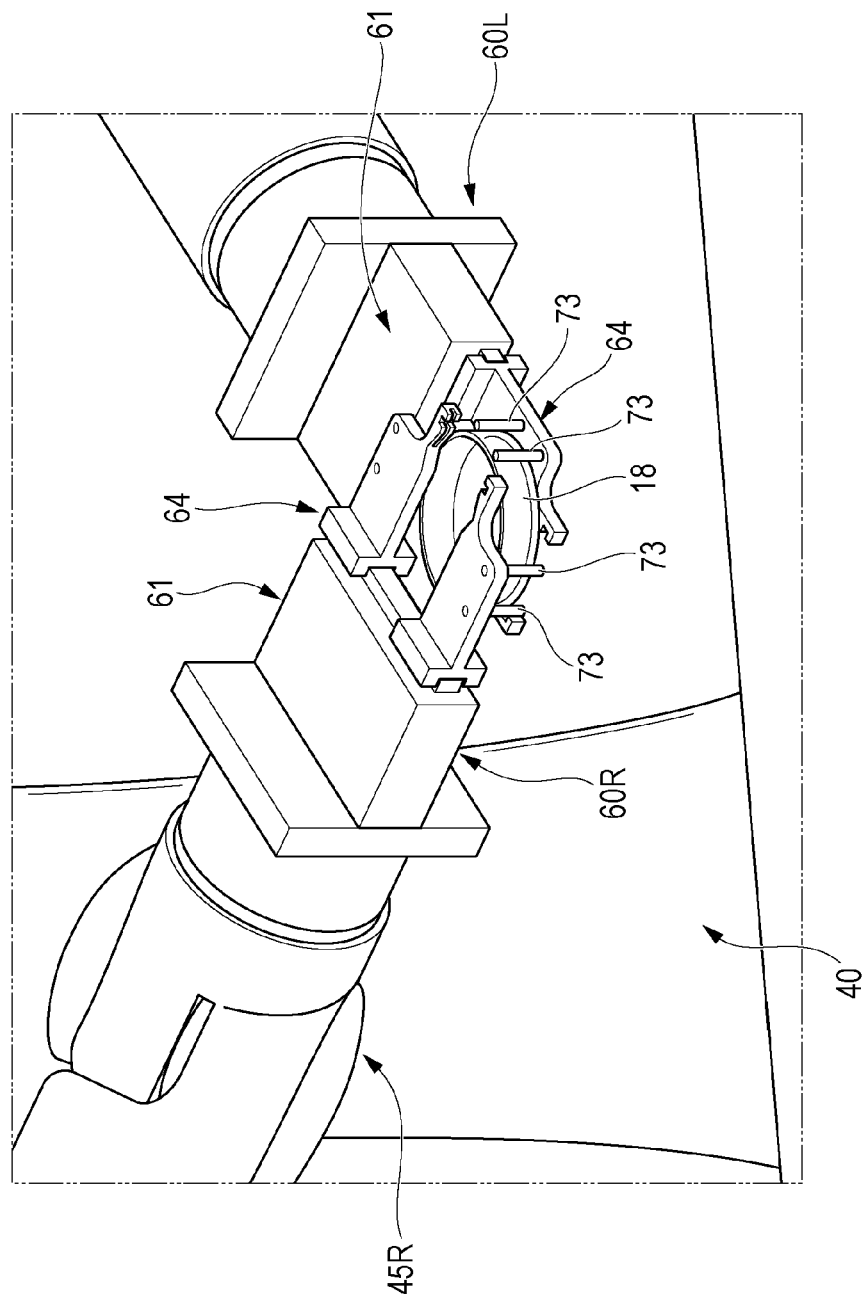
FIG. 16 is a diagram for describing the operation of the robot hand.

As illustrated in FIG. 16, the robot 40 controls the orientation of the first robot hand 60L so that the distal ends of the holding members 73 provided on the pair of bits 64 of the first robot hand 60L point upward. Also, the robot 40 opens the pair of bits 64 of the first robot hand 60L so that the space between the pair of bits 64 is slightly larger than the size of the culture vessel 18 that is held by the second robot hand 60R.

Subsequently, the second robot hand 60R places the culture vessel 18 inside the holding members 73 of the first robot hand 60L. After the culture vessel 18 is placed on the first robot hand 60L, the first robot hand 60L causes the gripper 61 to close the pair of bits 64 to hold the culture vessel 18. Thus, the first robot hand 60L holds the culture vessel 18 while supporting the bottom surface of the culture vessel 18 in the state in which the open side of the culture vessel 18 faces upward.

In this example, by passing the culture vessel 18 from the second robot hand 60R to the first robot hand 60L, the manner in which the culture vessel 18 is held can be changed from that in which the culture vessel 18 can be easily picked up from a flat surface to that in which a tool or the like can be easily inserted into the culture vessel 18 through the open side.

Next, an example in which an object to be held is held by the large-diameter holders 68 and 68-2 will be described.

Figure 5:
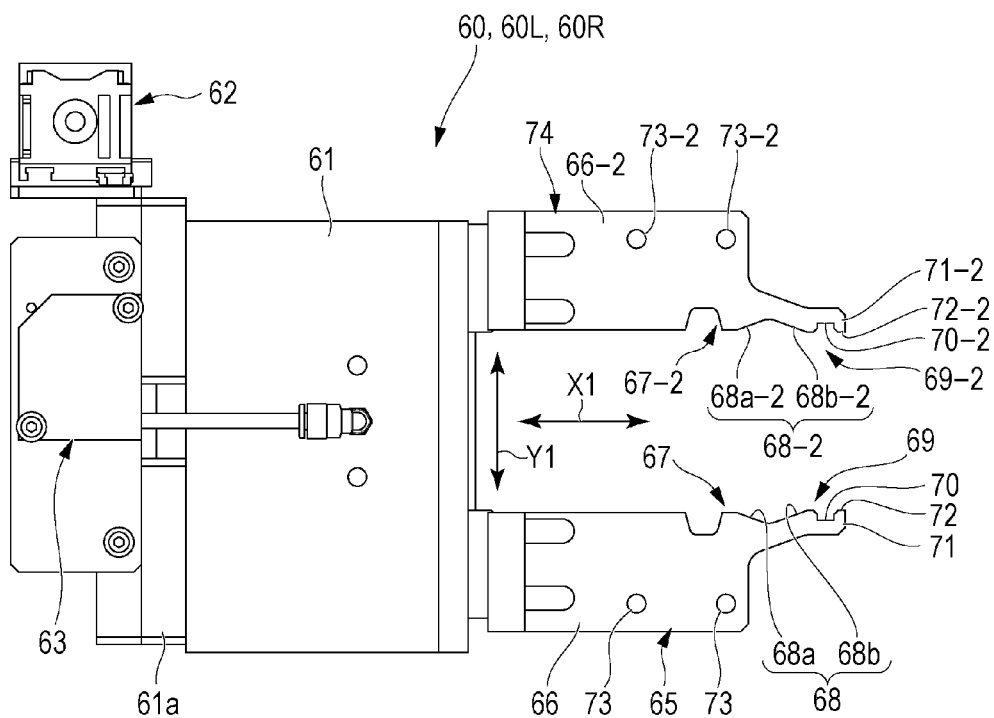
FIG. 5 is a plan view of the robot hand.
Figure 6:
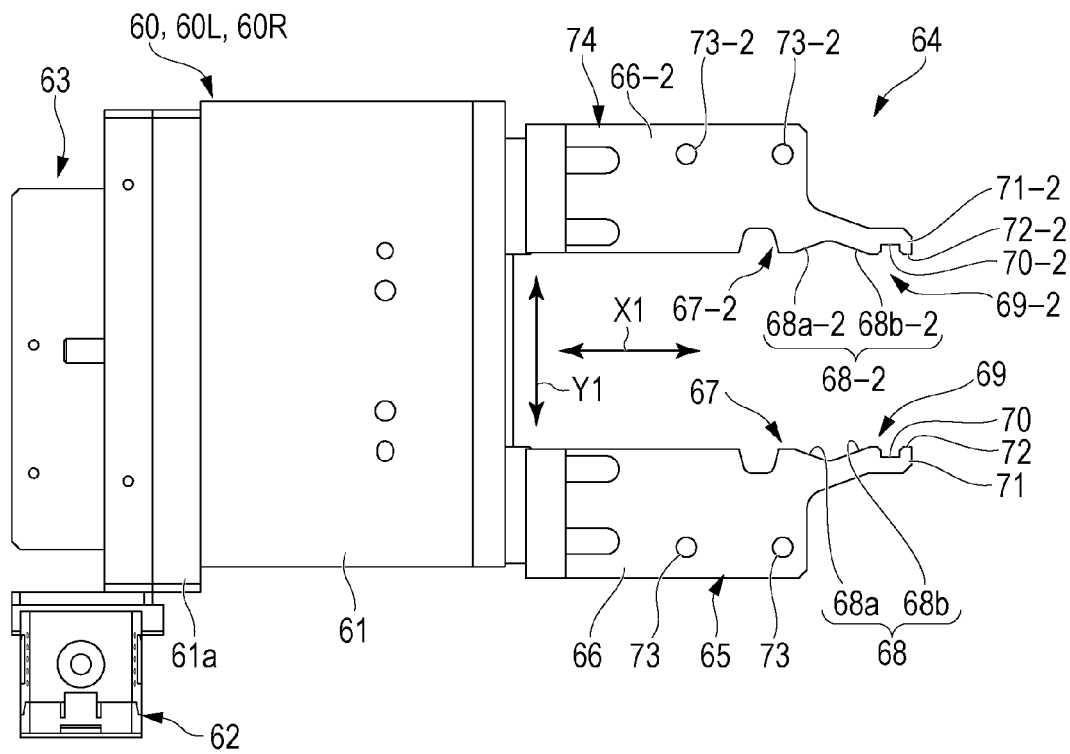
FIG. 6 is a bottom view of the robot hand.
Figure 7:
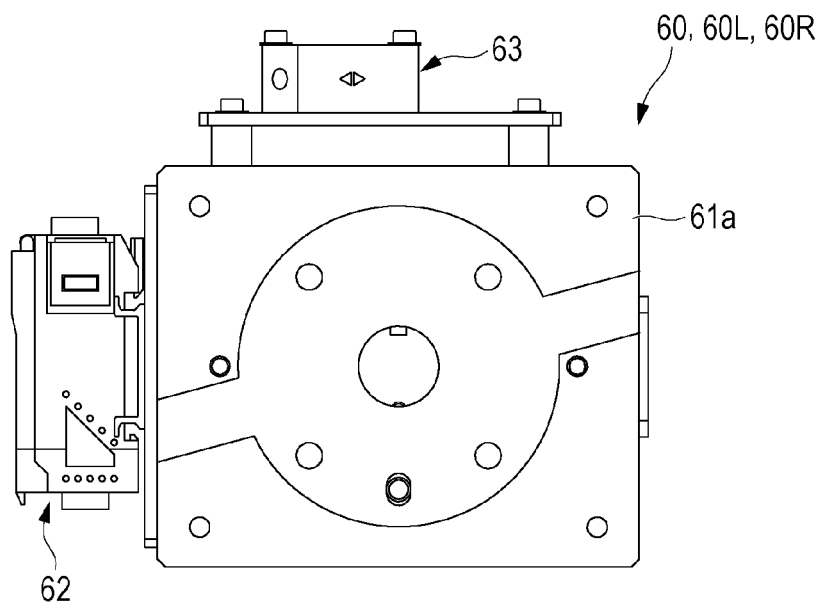
FIG. 7 is a left side view of the robot hand.
Figure 8:
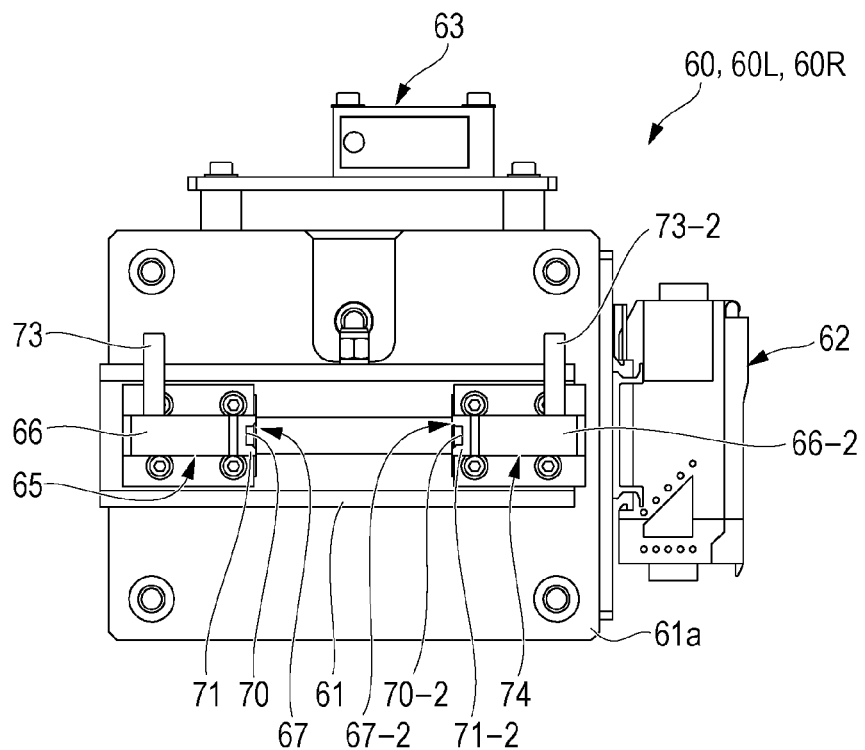
FIG. 8 is a right side view of the robot hand.
Figure 9:
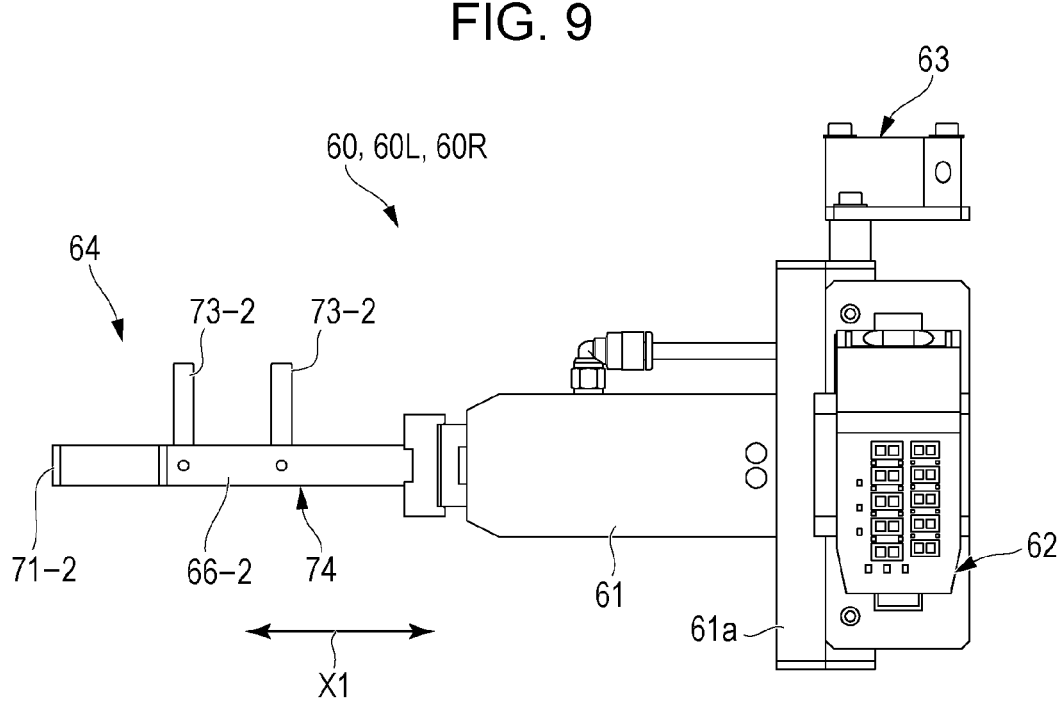
FIG. 9 is a rear view of the robot hand.

The first surfaces 68a and 68a-2 of the large-diameter holders 68 and 68-2, respectively, oppose each other, and the second surfaces 68b and 68b-2 of the large-diameter holders 68 and 68-2, respectively, also oppose each other (see FIG. 5). When the object to be held is held between the large-diameter holders 68 and 68-2, the outer peripheral surface of the object is supported by four surfaces, which are the first surfaces 68a and 68a-2 and the second surfaces 68b and 68b-2.

As described above, with the robot 40 and the robot hands 60 according to the present embodiment, the culture vessel 18 and the microtube 19 can be held in various manners by the pair of bits 64. Therefore, processes can be performed without replacing the robot hands, and loss of process time can be reduced.

There are snap-cap microtubes that are sealed by pushing caps into container bodies in which liquid is contained and screw-cap microtubes in which container bodies and caps are threaded. The caps of the snap-cap microtubes can be opened simply by snapping up the caps away from the container bodies, and therefore the snap-cap microtubes can be easily handled in the case where the snap-cap microtubes are manually handled. Integrally molded microtubes in which a container body and a cap are connected to each other with a hinge are an example of the snap-cap microtubes. The integrally molded microtubes can be manufactured at a lower cost than the screw-cap microtubes.

However, in the case where the microtubes are handled by robot hands, it has been difficult to snap up the caps without applying vibrations to the samples contained in the microtubes. Therefore, screw-cap microtubes have been used for robots that perform processes in which the influence of vibrations applied to the samples is not ignorable.

In contrast, with the robot hands 60 according to the present embodiment, the cap portion 19b is inserted into the rectangular recess 70 and pulled while the hinge 19c of the microtube 19 serves as a fulcrum. Therefore, the cap portion 19b that tries to flip open owing to the elasticity of the hinge 19c is retained by one of the pair of bits 64 that is in contact with the hinge 19c. Accordingly, the risk that the cap portion 19b will be suddenly opened and the microtube 19 will vibrate can be reduced, and vibrations are not easily applied to the sample contained in the microtube 19. As a result, adverse effects of the vibrations on the sample can be minimized.

Since the first robot hand 60L and the second robot hand 60R have the same shape, the left and right robot hands 60 can perform the same process. Therefore, processes can be appropriately performed even in a small work space in which the swingable range of the swing portion 44 is limited.

Since each of the first robot hand 60L and the second robot hand 60R includes the pair of bits 64, the microtube 19 can be passed between the first robot hand 60L and the second robot hand 60R so as to change the manner in which the microtube 19 is held. Thus, the manner in which the microtube 19 is held can be changed in a shorter time than in the case where the microtube 19 is once released and then held again in a different manner. In addition, the microtube 19 can be passed between the first and second robot hands 60L and 60R while the swing portion 44 is performing a swinging motion, so that the microtube 19 can be quickly conveyed between physicochemical instruments.

In addition, since the outer periphery of the bottom portion of the culture vessel 18 can be held by the four holding members 73, a wall portion that defines the outer peripheral surface of the culture vessel 18 does not receive a large force. Therefore, the culture vessel 18 can be prevented from being deformed or breaking.

In addition, according to the present embodiment, cap portions of snap-cap microtubes can be opened and closed. Therefore, the cost of consumable supplies can be made lower than that in the case where screw-cap microtubes are used.

Although the embodiment of the present disclosure has been described in detail with reference to the drawings, the detailed configuration is not limited to the embodiment, and design changes, etc., are included in the scope of the present disclosure.

The present disclosure may be applied to a robot hand and a robot.

It should be understood by those skilled in the art that various modifications, combinations, sub-combinations and alterations may occur depending on design requirements and other factors insofar as they are within the scope of the appended claims or the equivalents thereof.

What is claimed is:

1. A robot hand comprising:
   a pair of bits, the robot hand holding a microtube by causing the pair of bits to perform an opening-closing operation, the pair of bits having a lug that comes into contact with an outer peripheral surface of a container body of the microtube or an outer peripheral surface of a cap portion of the microtube as a result of the opening-closing operation, and a recess in which both a part of the cap portion and a part of a flange of the microtube are inserted while the lug is in contact with the outer peripheral surface of the container body,
   wherein the recess has a rectangular shape and includes a pair of surfaces between which the cap portion and the flange are disposed, and wherein the pair of bits is closed while a corner of the recess is in contact with the outer peripheral surface of the container body to retain the microtube in an orientation different from an orientation of the microtube in the state in which the cap portion is inserted in the recess.

2. The robot hand according to claim 1,
wherein the microtube is a snap-cap microtube in which the container body and the cap portion are connected to each other with a hinge, and
wherein the cap portion of the microtube that is held by a tube rack while being closed with the cap portion is pulled off from the container body by engaging a part of the cap portion that is located opposite the hinge with the recess, bringing a part of the pair of bits other than the recess into contact with the hinge, and using the hinge as a fulcrum, or
the cap portion of the microtube that is held by the tube rack with the cap portion detached from the container body is pushed into the container body by pushing the cap portion with the pair of bits so as to bend the hinge and further pushing a part of the cap portion with the pair of bits.

3. The robot hand according to claim 1,
wherein the recess is formed in each of the pair of bits so that the recesses oppose each other,
wherein the cap portion and the flange are inserted into each of the recesses with a predetermined clearance in a thickness direction of the cap portion, and
wherein the pair of bits holds the microtube in a state such that a gap is provided between the lug and the outer peripheral surface of the container body in a process of stirring liquid contained in the microtube by applying vibration to the microtube.

4. The robot hand according to claim 1,
wherein the pair of bits includes four rod-shaped holding members that have a length greater than or equal to an external dimension of a culture vessel in a depth direction of the culture vessel,
wherein two of the holding members are arranged parallel to each other on each of the pair of bits,
wherein distal ends of the holding members are on the same imaginary plane, and
wherein the holding members are arranged so as to surround an outer periphery of the culture vessel by moving the holding members in a direction from an open side to a bottom side of the culture vessel, and the pair of bits is closed, so that an outer periphery of a bottom portion of the culture vessel is held by the distal ends of the holding members and an outer peripheral surface of the culture vessel is held by outer peripheral surfaces of portions of the holding members on a proximal side of the distal ends.

5. A robot comprising the robot hand according to claim 1.

6. A robot comprising:
the robot hand according to claim 1; and
a second robot hand having the same shape as the robot hand,
wherein an object to be held is passed between the robot hand and the second robot hand to change a manner in which the object is held.

7. The robot according to claim 6, further comprising:
a first arm to which the robot hand is attached and which has at least six or more degrees of freedom; and
a second arm to which the second robot hand is attached and which has at least six or more degrees of freedom.

* * * * *